United States Patent [19]

Sih

[11] 4,311,835
[45] Jan. 19, 1982

[54] 2-DECARBOXY-2-TETRAZOLYL-19-HYDROXY-6A-CARBA-PGI$_1$ COMPOUNDS

[75] Inventor: John C. Sih, Kalamazoo, Mich.

[73] Assignee: The Upjohn Company, Kalamazoo, Mich.

[21] Appl. No.: 126,486

[22] Filed: Mar. 3, 1980

Related U.S. Application Data

[62] Division of Ser. No. 54,811, Jul. 5, 1979, Pat. No. 4,225,508.

[51] Int. Cl.$^3$ .................. C07D 257/04; A61K 31/41

[52] U.S. Cl. .................. 542/429; 548/253; 424/269

[58] Field of Search .................. 548/253; 542/429

Primary Examiner—Donald G. Daus
Assistant Examiner—D. B. Springer
Attorney, Agent, or Firm—L. Ruth Hattan; Robert A. Armitage

[57] ABSTRACT

The present invention provides novel 2-decarboxy-2-tetrazolyl-19-hydroxy-6a-carba-PGI$_1$ sulfonylamides which are useful for pharmacological purposes, e.g., anti-asthmatic indications.

1 Claim, No Drawings

2-DECARBOXY-2-TETRAZOLYL-19-HYDROXY-6A-CARBA-PGI₁ COMPOUNDS

CROSS REFERENCE TO RELATED APPLICATION

The present invention is a divisional application of U.S. Ser. No. 54,811, filed 5 July 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-tetrazolyl-19-hydroxy-6a-carba-PGI$_2$ compounds. The novel prostacyclin analogs are useful for pharmacological purposes, e.g., as anti-asthmatic agents. The preparation and use of these compounds is incorporated here by reference from U.S. Pat. No. 4,225,508.

PRIOR ART

For background on prostacyclin, see for example R. A. Johnson, et al., Prostaglandins 12, 915-928 (1976) and R. A. Johnson, et al., J. Am. Chem. Soc. 100, 7690-7704 (1978), and, as to pharmacological activity, the references cited therein. For analogs of prostacyclin, see, for example, J. Fried, et al., Proc. Natl. Acad. Sci. U.S.A. 74 2199–2203, K. C. Nicolaou, et al., J.C.S. Chem. Comm. 1977, 331-332, N. A. Nelson, J. Am. Chem. Soc. 99, 7362-7363 (1977), and K. Kojima, et al., Tetra. Letters, 1978, (1977), and K. Kojima, et al., Tetra. Letters, 1978, 3743-3746. Regarding the nomenclature for analogs of PGI$_2$, see R. A. Johnson, et al., Prostaglandis 15, 737-740 (1978).

SUMMARY OF THE INVENTION

The present invention particularly provides a prostacyclin-type compound of the formula

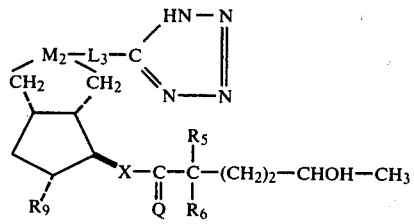

wherein L₃ is
(1) —(CH₂)$_n$—, wherein n is one to 5, inclusive,
(2) —(CH₂)$_p$—CF₂—, wherein p is 2, 3, or 4, or
(3) —CH₂—CH=CH—;
wherein M₂ is

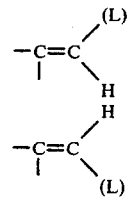

wherein Q is oxo, α-H:β-H, α-OH:β-R₄, or α-R₄:β-OH,
wherein R₄ is hydrogen or alkyl of one to 4 carbon atoms, inclusive,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;
wherein R₉ is hydrogen or hydroxyl; and
wherein X is
(1) trans—CH=CH—,
(2) cis—CH=CH—,
(3) —C≡C—, or
(4) —CH₂CH₂—.

I claim:
1. A prostacyclin-type compound of the formula

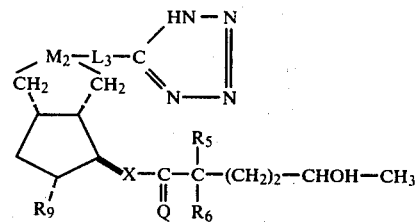

wherein L₃ is
(1) —(CH₂)$_n$—, wherein n is one to 5, inclusive,
(2) —(CH₂)$_p$—CF₂—, wherein p is 2, 3, or 4, or
(3) —CH₂—CH=CH—;
wherein M₂ is

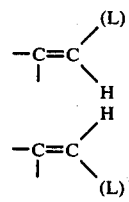

wherein Q is oxo, α-H:β-H, α-OH:β-R₄, or α-R₄:β-OH,
wherein R₄ is hydrogen or alkyl of one to 4 carbon atoms, inclusive,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;
wherein R₉ is hydrogen or hydroxyl; and
wherein X is
(1) trans—CH=CH—,
(2) cis—CH=CH—,
(3) —C≡C—, or
(4) —CH₂CH₂—.

* * * * *